United States Patent [19]
Frank et al.

[11] Patent Number: 5,246,013
[45] Date of Patent: Sep. 21, 1993

[54] PROBE, SYSTEM AND METHOD FOR DETECTING CARTILAGE DEGENERATION

[75] Inventors: Eliot H. Frank, Cambridge; Evan P. Salant, Boston; Alan J. Grodzinsky, Lexington, all of Mass.

[73] Assignee: Massachusetts Institute of Technology, Cambridge, Mass.

[21] Appl. No.: 817,747

[22] Filed: Jan. 7, 1992

Related U.S. Application Data

[63] Continuation-in-part of Ser. No. 455,623, Dec. 22, 1989, abandoned.

[51] Int. Cl.$^5$ .............................................. A61B 5/103
[52] U.S. Cl. .................................................... 128/774
[58] Field of Search ................ 128/774, 779, 781, 782

[56] References Cited

U.S. PATENT DOCUMENTS

| | | | |
|---|---|---|---|
| 4,361,154 | 11/1982 | Pratt, Jr. | 128/660 |
| 4,754,763 | 7/1988 | Doemland | 128/739 |

OTHER PUBLICATIONS

Sachs et al., "An Electromechanically Coupled Poroelastic Medium Driven by an Applied Electric Current: Surface Detection of Bulk Material Properties" PCH PhysicoChemical Hydrodynamics, vol. 11, No. 4, pp. 585–614 (1989).
Grodzinsky, "Electromechanical and Physicochemical Properties of Connective Tissue", CRC Critical Reviews in biomedical Eng., 9(2): 133–99 (1983).
Frank et al., Streaming Potentials: A Sensitive Index of Enzymatic Degradation in Articular Cartilage:, J. Ortho, Res., 5:497–508 (1987).
Frank et al., "Cartilage Electromechanics—I. Electrokinetic Transduction and the Effects of Electrolyte pH and Ionic Strength", J. Biomechanics, 20(6): 615–27 (1987).
Frank et al., "Carilage Electromechanics—II. A Continuum Model of Cartilage Electrokinetic and Correlation with Experiments", J. Biomechanics, 20(6):629–39 (1987).

*Primary Examiner*—William E. Kamm
*Attorney, Agent, or Firm*—Hamilton, Brook, Smith & Reynolds

[57] ABSTRACT

A surface probe is disclosed for use in detecting the degree of degeneration in mammalian tissue. The surface probe comprises in combination with each other surface probe means for applying to a surface of the mammalian tissue a force which affects an electrokinetic parameter indicative of the amount of charged specie involved in tissue degeneration and surface detection means for detecting the electrokinetic parameter at the same surface of the mammalian tissue. A method is disclosed for detecting the degree of degeneration in mammalian tissues. Further, a system for diagnosing degenerative changes in cartilage tissue is disclosed. The system discloses a waveform generator as a source of current connected with connectors for transmitting electrical current between the generator and the surface electrodes of the surface probe and a computer connected by connectors to surface electrodes and transmitting electrodes in the surface probe for controlling electromechanical input to the surface electrodes and processing electromechanical output from the transmitting electrodes.

17 Claims, 7 Drawing Sheets

PROBE, SYSTEM AND METHOD FOR DETECTING CARTILAGE DEGENERATION

This application is a continuation-in-part of U.S. patent application Ser. No. 07/455,623 filed on Dec. 22, 1989, now abandoned.

BACKGROUND OF THE INVENTION

Cartilage is a biological tissue which functions by providing a load-bearing, low-friction surface necessary for normal joint operation. The structure of this tissue is composed of a sparse population of cells and a large extracellular matrix (ECM). It is the ECM which allows cartilage to accommodate physiological mechanical loading of the joint. The ECM is composed principally of a hydrated collagen fibril network enmeshed in a gel of highly charged proteoglycan molecules. Proteoglycans are responsible for providing a high fixed charge density which contributes significantly to the overall compressive stiffness of cartilage necessary for normal joint function.

Osteoarthritis is a degenerative joint disease, affecting over 40 million Americans. During motion and weight bearing, osteoarthritis causes significant pain in disease affected individuals. One of the earliest events in osteoarthritis is a molecular level alternation of the cartilage extracellular matrix, and loss of highly charged proteoglycan macromolecules from the matrix. Since the ability of cartilage to withstand compressive loading is due mostly to the presence of proteoglycans, loss of these molecules makes the tissue softer and more susceptible to further wear and degradation. These molecular level changes often occur in very localized regions of cartilage along the joint surface, and occur non-uniformly with depth in the tissue.

The current technologies used for diagnosing such degenerative changes in cartilage matrix, such as x-rays, magnetic resonance imaging and visual inspection by arthroscopy, detect disease at relatively advanced, and probably irreversible, stages. Unfortunately, detection of early degenerative changes, when therapeutic intervention might be most beneficial, is not presently available. Thus, there is a need for the early quantitative assessment of degenerative changes in cartilage.

SUMMARY OF THE INVENTION

A surface probe for use in detecting the degree of degeneration in mammalian tissue comprises in combination with each other surface probe means for applying to a surface of the mammalian tissue a force, which affects an electrokinetic parameters, and surface detection means for detecting the electrokinetic parameter. The force affects an electrokinetic parameter indicative of the amount of charged species involved in tissue degeneration and surface detection means for detecting the electrokinetic parameter at the same surface of the mammalian tissue.

A method for detecting the degree of degeneration in mammalian tissues comprises applying to a surface of the mammalian tissue a force. The force affects an electrokinetic parameter indicative of the amount of charged species involved in tissue degeneration of the mammalian tissue. Further, the method includes detecting the electrokinetic parameter at the same surface of the mammalian tissue an comparing the detected electrokinetic parameter values to a normal value for the tissue previously measured from clinically normal tissue.

A planar, multilayered, surface probe for diagnosing degenerative changes in cartilage tissue comprises surface electrodes with an interdigitating grid of conductive material for application of electrical current to a cartilage surface. The surface probe has a first insulating sheet with its lower surface metalized for electrical grounding and the surface electrodes bonded to the upper insulating surface of the first insulating sheet. Further, the surface probe has a second insulating sheet bonded to the metalized side of the first insulating sheet, a piezoelectric polymeric film for transduction of mechanical stress to electrical current, bonded to the second insulating sheet and electrodes bonded to the film for transmitting electrical current generated by the piezoelectric polymeric film to a detector.

A system for diagnosing degenerative changes in cartilage tissue comprises a surface probe with a waveform generator as a source of current connected with connectors for transmitting electrical current between the generator and the surface electrodes of the surface probe. Further, the system has a computer connected by connectors to surface electrodes and transmitting electrodes in the surface probe for controlling electromechanical input to the surface electrodes and processing electromechanical output from the transmitting electrodes.

This invention offers sensitivity and specificity for detection of changes in electrokinetic parameters of mammalian tissue due to degeneration.

DETAILED DESCRIPTION OF THE INVENTION

The above features and other details of the surface probe system and methods of this invention will now be more particularly described with relevance to the accompanying drawings and pointed out in the claims. It will be understood that the particular embodiments of the invention are shown by way of illustration and not as limitations of the invention. The principle feature of this invention can be employed in various embodiments without departing from the scope of the invention.

Cartilage and Connective Tissue

Articular cartilage is the dense connective tissue that functions as a load-bearing material in synovial joints. Cartilage from adult animals and humans is without vascular, nervous or lymphatic components. (Mankin et al., *Osteoarthritis*. Ed. Moskowitz, W. B. Saunders, Philadelphia, pps. 43–80 (1984)). The tissue's sparse population of cells derives its nutrition primarily from the synovial fluid (Mankin et al., Ibid; McKibbin et al., *Adult Articulate Cartilage*, Ed. Freeman MAR, Pittman Medical, Kent, U.S., pps 461–486 (1979). The cells are responsible for the synthesis, maintenance and gradual turnover of an extracellular matrix (ECM) composed principally of hydrated collagen fibrils and highly charged proteoglycan molecules (Hay, *Cell Biology of Extracellular Matrix*, Plenum Press, N.Y. (1981)). The osmotically swollen ECM (20–30% of tissue wet weight) and the tissue's high water content (70–80% of wet weight) are responsible for the complex porelastic behavior of cartilage that characterizes its normal response to transient (Mow et al., *General Biomechanics*, 17:377–394 (1984)) and cyclic (Lee et al. *J. Biomechanical Eng.*, 103:280–292 (1981); Torzilli, P. A., *Mechanics Res. Comm.*, 11:75–82 (1984)) loads.

Electrokinetic Transduction

When cartilage is compressed, a mechanical-to-electrical transduction occurs resulting in measurable electrical potential (Bassett et al., *Science*, 178:982–983 (1972); Lotke et al., *J. Bone Joint Surg.*, 56A:1040–1046 (1974); Grodzinsky et al., *Nature*, 275:448–450 (1978)). Results involving transient stress relaxation (Grodzinsky et al., Ibid) and sinusoidal deformation of cartilage in uniaxial contained compression (Lee et al., Ibid; Grodzinsky et al. Ibid) suggested that an electrokinetic effect called the streaming potential was the primary mechanism for this mechanical-to-electrical transduction in cartilage. The electrokinetic streaming potential is defined as follows: mechanical deformation of cartilage and other soft tissues containing charged, hydrated ECM causes a flow of interstitial fluid and entrained counterions relative to the fixed charge groups of the ECM (Anderson et al., *Nature*, 218:166–168 (1968); Grodzinsky et al., Ibid). Fluid convection of counterions tends to separate these ions from the oppositely charged molecules of the ECM. This charge separation produces an electric field collinear to the fluid flow and proportional to the fluid velocity at each position within the ECM. The open-circuit voltage thus produced is called the streaming potential. The amplitude and phase of the measured potential compares well to that predicted by a theory combining sinusoidal electrokinetic transduction (Lee et al., Ibid; Grodzinsky, et al., Ibid) and cartilage fluid flow (Mow et al., Ibid), further confirming the steaming potential hypothesis.

The Relation of Electrokinetic Transduction to Tissue Composition in Healthy and Diseased States All ionized macromolecules can theoretically contribute to electrokinetic transduction, including those in the ECM. At physiological pH, collagen contains nearly equal numbers of ionized amino and carboxyl groups, and hence possesses little or no net fixed charge (Bowes et al., *Biochemistry J.*, 43:358–365 (1948); Li et al., Biopolymers, 15:1439–1460 (1976)). At pH values less than 5.0 or greater than 9.5, collagen molecules attain a positive or negative net fixed charge, respectively, and collagen fibrils swell laterally increasing their intrafibrillar water content (Glimcher et al., *Treatise on Collagen*, Ed. Gould, Academic Press, N.Y. pps. 68–251 (1968); Nussbaum et al., *J. Membrane Sci.*, 8:193–219 (1981); Torzilli, *J. Ortho. Res.*, 3:473–483 (1985)). Collagen can then contribute appreciably to electrokinetic effect provided that fluid flow through and around the individual fibrils of cartilage type II collagen (Grynpas et al., *Biochem. Biophys. Acts*, 626:346–355 (1980)) is substantial.

Figure 1:
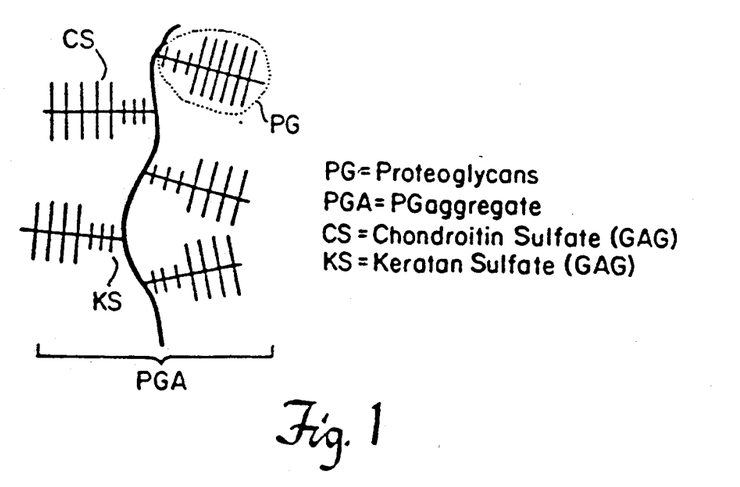
FIG. 1 is a schematic representation of a proteoglycan aggregate (PGA), illustrating the structural relationship of its components.

The proteoglycans (PG), whose structure and function have been extensively reviewed (Muir, *The Joints and Synovial Fluid*, Ed. Sokoloff, Academic Press, N.Y., pps. 28–94 (1980); Hascall et al., *Cell Biology of Extracellular Matrix*, Ed. Hay, Plenum Press, N.Y., pps. 39–64 (1981)) contribute the major source of fixed charge to electrokinetic interactions at physiological pH. As seen schematically in FIG. 1, proteoglycan charge groups are located predominantly on the chondroitin sulfate (CS) and keratin sulfate (KS) glycoaminoglycan chains that are covalently linked to the protein core of the proteoglycan monomer (Hascall et al., Ibid; Muir, Ibid). The chondroitin sulfate chain (M.W. 20,000) is a linear array of 20–60 disaccharides, each of which contains one ionized sulfate group (on the galactosamine moiety) and one carboxyl group, on the average. Keratin sulfate chains contain 5–10 disaccharides, each contributing one sulfate group (on the glycosamine moiety). The proteoglycan monomers, in turn, form large aggregates in cartilage (Muir, Ibid). The resulting fixed charge density of normal cartilage is as high as 0.1–0.2 mol per liter of tissue fluid (Maroudas, *Adult Articulate Cartilage*, Ed. Freeman, Pittman Medical, Kent, U.K., pps 215–290 (1979). Proteoglycan charge groups are known to be responsible for the high Donnan osmotic swelling pressure (Maroudas, Ibid) that enables healthy cartilage to electromechanically resist compressive loads in normal joints.

Electrokinetic transduction in cartilage originates in the fixed charge groups of the proteoglycans of the tissues extracellular matrix. These charged groups are ionized under physiological conditions in vivo, and over a wide rang of both pH and ion content in vivo (Maroudas, Ibid: Grodzinsky, *CRC Critical Reviews Biomedical Eng.*, 9:133–199 (1983)). Mobile electrolyte counterions within the tissue, together with these fixed charge groups, form electrical double layers whose properties are determined by the local chemical environment (pH and ionic strength). Mechanical deformation or fluid steaming within the tissue tends to separate the mobile ions from the fixed charge groups, giving rise to voltages called streaming potentials, as mentioned earlier. Conversely, an applied electric field can exert a force on the ionic space charge in the fluid phase, which causes an electroosmotic convection of fluid. The applied field also produces concomitant electrophoretic motion of the negatively charged solid matrix. These electroosmotic and electrophoretic effects can result in mechanical deformations and stress within the tissue. In other words, the net negative charge density of the proteoglycans matrix impacts to the surrounding fluid a net positive charge. The application of a current across the cartilage imparts an electrophoretic force on the proteoglycans and an oppositely directed force on the positively charged fluid. In confined area, such as cartilage, the resulting redistribution of fluid and solid generated by the uniform current induces a mechanical stress. This stress can be measured by a mechanical transducer.

Use of Electrokinetic Phenomena to Detect Cartilage Degradation

Figure 2:
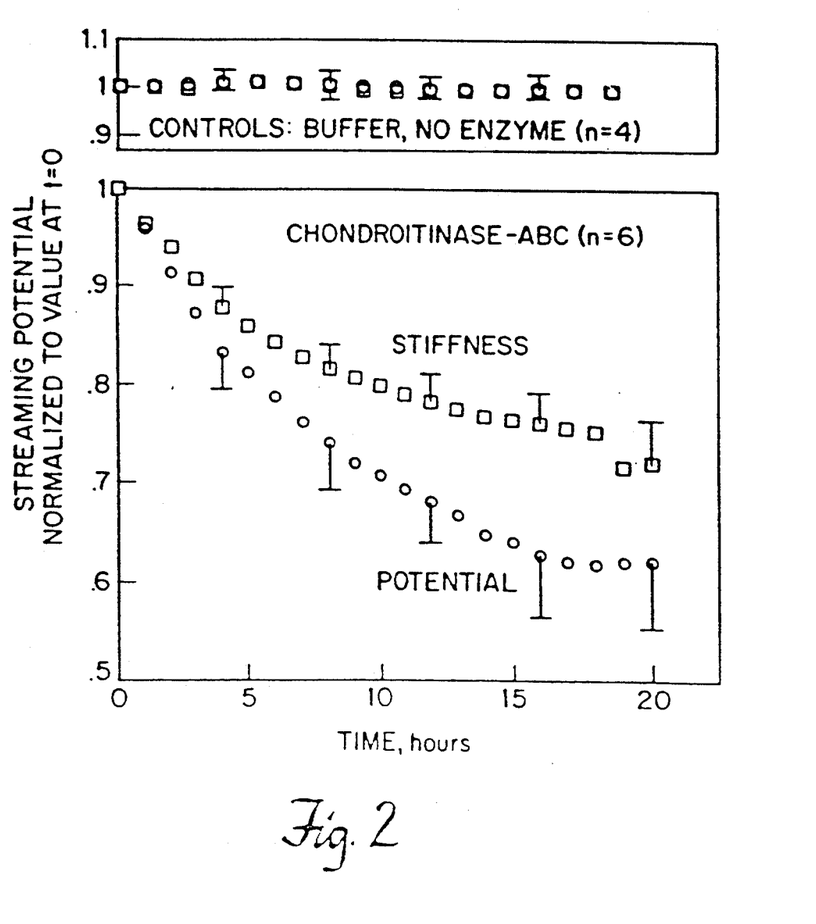
FIG. 2 is a graphic representation of the decrease in detected electrical streaming potential with time, after enzymatic removal of proteoglycans from cartilage.

A hallmark of degenerated cartilage is the loss of the highly charged proteoglycans which are responsible for the high fixed charge density of the tissue under physiological conditions. FIG. 2 graphically illustrates the effect of enzymatic digestion on cartilage as a model system of cartilage degeneration (Frank et al., J. Ortho. Res, 5:497-508 (1987). Digestion with chondroitinase removes the highly charged chondroitin sulfate groups from the proteoglycans in the extracellular matrix. The loss of the charge density in the matrix results in a significant decrease in the compressive stiffness and the streaming potential of the tissue. Such enzymatic extractions have a proportionally larger effect on the streaming potential than the stiffness, since loss of all charge groups would ideally decrease the potential to zero but would not eliminate the contribution of the remaining solid content to the tissue's stiffness. Chondroitinase does result in a more dramatic decrease in steaming potential than mechanical stiffness. The relative change in streaming potential and stiffness would depend on the specific matrix constituents that are degraded.

The detected mechanical stress produced by an applied current, or the electrical streaming potential produced by an applied mechanical displacement is used to infer the compositionally-dependent properties of cartilage. To accomplish this, a theoretical model that was previously developed for one dimensional electromechanical transduction in connective tissues (Frank et al., J. Biomechanics, 20(6):629-639 (1987)) is adapted for the three dimensional geometry (Sachs et al., Physicochemical Hydrodynamics, (1989)) associated with the probe. This model is used to compute the electromechanical coupling coefficients, the equilibrium elastic moduli, hydraulic permeability, and electrical conductivity of cartilage (or other tissue) from the detected signals. Previous literature has demonstrated that these intrinsic mechanical and electromechanical properties of cartilage are directly dependent on the content and organization of extracellular matrix molecules; the electromechanical coupling coefficients have proven to be the most sensitive indicators of cartilage degeneration (Frank et al., J. Orthop. Res., 5:497-508 (1987)).

The theoretical model relates the effects of macroscopic deformations on fluid flow and electrokinetic transduction in cartilage. It is convenient to average over molecular dimensions and consider macroscopically smoothed volumes. This macrocontinuum approach essentially combines laws for linear electrokinetic transduction in ionized media with the principles of the linear biphasic theory for cartilage (Mow et al., J. Biomech. Eng., 102:73-84 (1980). The biphasic theory highlights the significance of fluid flow to the rheological behaviors of cartilage.

A constitutive law for the total stress $T_{ij}$ in a homogeneous, isotropic tissue valid for small strains $\epsilon$, is $$T_{ij} = 2G(c)\epsilon_{ij} + (\lambda(c)\epsilon_{kk} - P_f)\delta_{ij} \tag{1}$$

where $P_f$ is the fluid pressure, the Lame constants G and $\lambda$ are functions of the ionic content of the cartilage (c) and $\delta_{ij}$ is the Kronecker delta function.

For the case of incompressible fluid and solid constituents, continuity relates the local fluid and solid velocities, $v_f$ and $v_s$, respectively (Armstrong et al., vol. pps (1984)).

$$\phi \cdot \nabla \cdot v_f + (1-\phi)\nabla \cdot C_s = 0 \tag{2}$$

where $\phi$ is the porosity. The total area-averaged relative fluid velocity, U, which is relevant to electrokinetic transduction, is defined by $$U = \phi(v_f - v_s). \tag{3}$$

Conservation of momentum takes the form $$\nabla \cdot T = 0 \tag{4}$$

where inertial effects can be ignored.

Linear, macroscopic laws for electrokinetics of isotopic media are used to relate the total area-averaged relative fluid velocity U and the current density J in the tissue to the gradients in fluid pressure P, and electrical potential V, $$\begin{bmatrix} U \\ J \end{bmatrix} = \begin{bmatrix} -k_{11} & k_{12} \\ k_{21} & -k_{22} \end{bmatrix} \begin{bmatrix} \nabla P_f \\ \nabla V \end{bmatrix} \tag{5}$$

where $k_{11}$ is the "short-circuit" hydraulic permeability, $k_{12}$ and $k_{21}$ are the electrokinetic coupling coefficients, the $k_{22}$ is the electrical conductivity. The coupling coefficients are equal by Onsager reciprocity ($k_{12} = k_{21}$), and can be expressed in terms of the charge density or (-potential ("zeta" potential) at the electrokinetic slip plane related to the pore wall surface charge of the cartilage extracellular matrix using microscopic continuum models for cartilage (Eisenberg et al., J. Ortho. Res., 3:148-159 (1985)). For materials like cartilage in which the fixed charge density is negative, $k_{12}$ and $k_{21}$ are defined as negative.

Finally, conservation of current states that the current density J has zero divergence for all frequencies of interest.

$$\nabla \cdot J = 0. \tag{6}$$

Two additional relations, important to specifying all quantities in three dimensions, are obtained by taking the curl of Equation (5).

$$\nabla \times J = 0. \tag{6}$$

and $$\nabla \times U = 0. \tag{8}$$

Equations (1) to (8) constitute the general three-dimensional theory of electromechanical transduction.

This theory can be solved for the specific geometry of the probe, and applied to either the case of current-generated mechanical stress or displacement-generated electrical streaming potentials.

Operation of the Surface Probe and System

The present invention measures electromechanical properties specific to tissues containing charged macromolecules by applying to the surface of the tissue an excitation (either electrical or mechanical) while simultaneously detecting the electrokinetic response (either mechanical or electrical, respectively). Specifically, the probe measures electromechanical properties by one of two alternative methods: 1) applying an electric current via surface electrodes and measuring the resulting current generated stress via a force transducer; or 2) applying a mechanical stress via a force transducer and measuring the mechanically generated streaming potential via surface electrodes. The excitation is time varying and also space varying along the surface. The tissue electrokinetic response to the excitation is also time varying and space varying along the surface and proportional to the amount of charged macromolecules within the tissue.

In cases where electrical current is applied, the design and function of probe is critical to the electric current density in the tissue. The applied current density drives electroosmosis of the fluid and electrophoresis of the solid within the tissue, resulting in a buildup in pressure which in turn is measured as the current generated stress. The distribution of current within the tissue is a function of effective wavelength (twice the distance between two adjacent electrode strips of the interdigitating grid). Simply stated, if the stimulating electrodes are relatively close together compared to the cartilage thickness ($\lambda << \delta$), the current field can only penetrate to a depth within the tissue approximately equal to the electrode separation. On the other hand, for widely spaced electrodes ($\lambda >> \delta$), the current density penetrates to the full thicknesses of the tissue. Thus by varying the wavelength, one can effectively probe varying depths into the cartilage.

Figure 3:
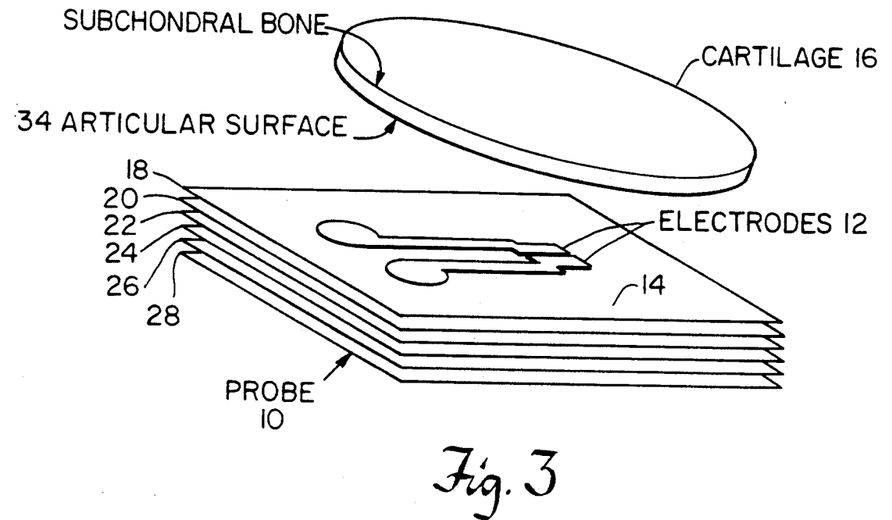
FIG. 3 is a schematic view of one embodiment of a diagnostic surface probe according to this invention and cartilage.

As illustrated in FIG. 3, surface probe 10 is constructed as a self-contained unit with electrodes 12 on the open face 14 of probe 10 which is applied to cartilage 16. In addition, probe 10 consists of individual layers of adhesive 18, metalized insulator layer 20, first adhesive 22, insulator layer 24, second adhesive 26, and electromechanical transducer 28. Open face 14 of probe 10 with surface electrodes is applied to the articular surface 34 of cartilage 16.

The practical limitations for probe dimensions relate to designing it for passage through an arthroscopic probe. Of course, the dimensions of the probe employed in other applications depend on the particular use. The constraints on the quantity of applied current density lies between the amount of current sufficient to provide a response but not enough to damage the cartilage.

Figure 4:
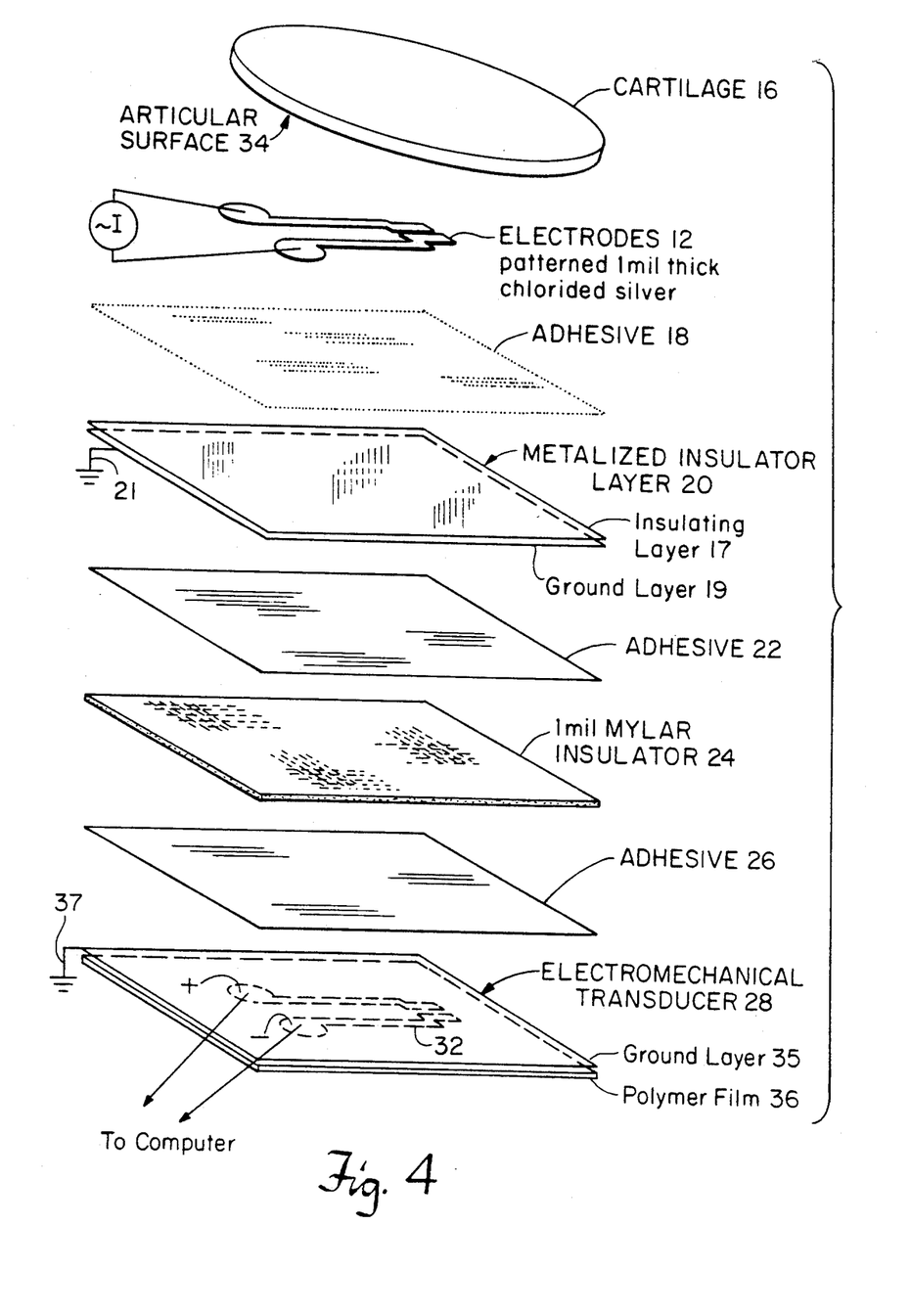
FIG. 4 is an exploded schematic view of one embodiment of a diagnostic surface probe.

FIG. 4 illustrates the individual components of the surface probe in relationship to one another. Electrodes 12 are bonded by adhesive 18 to metalized insulator layer 20 which has insulating layer 17 and ground layer 19 connected to ground means 21 which can consist of a Mylar ® brand polyester film shield with its lower surface metalized. This, in turn, is bonded by first adhesive 22 to insulator layer 24. In one embodiment, insulator layer 24 is a 1 ml thick Mylar ® brand polyester film insulation, which is bonded by second adhesive 26 to electromechanical transducer 28. The restraints which affect the choice of electrodes 12 include ease of fabrication and the need to minimize or eliminate deleterious chemical reaction products associated with the passage of electric current. Electrodes can be made of a metal or a metal salt. In one embodiment, thin chlorided silver strips, 1 mil thick, are easily fabricated into an interdigitated array for excitory electrode 30 as diagrammed in FIG. 5. The same pattern of interdigitated electrodes such as these chlorided silver strips can also be used for electromechanical transducer electrodes 32. Mechanical transducer 28 which can consist of Kynar PVDF ® brand piezo film (52 $\mu$m thick) is bonded by second adhesive 26 to insulation layer 24. finally, to piezoelectric film, which has ground layer 35 attached to ground means 37, and polymer film 36 is bonded an array of a metal or a metal salt, such as electrodes 32. In one embodiment, silver chloride strips are used as sensing electrodes 32. A commercially available piezo electric film which has an appropriate dynamic range of $10^{-5}$ to $10^8$ N/m$^2$ and a broad band frequency response from dc to 1 GHz can be used. In addition, a patterned electrode array of this film can be fabricated with a strip width as smal) as 25 $\mu$m and inter-strip spacing of 100 $\mu$m. Since cartilage thickness varies, a series of arrays can be fashioned to probe short, middle and long wave responses. Alternatively, a single, interdigitated multi-strip electrode array can be controlled by the computer to deliver currents over a wide range of spatial wavelengths. The components and construction of this embodiment of probe 10 meet the experimental parameters which define that there is no vertical motion of the solid matrix of the cartilage at the cartilage-probe interface and no relative normal fluid flow at the cartilage-probe interface.

Figure 5:
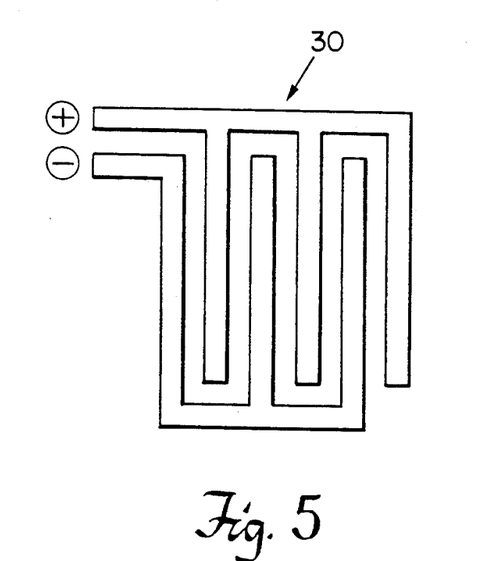
FIG. 5 is a plan view is an interdigitating electrode pattern.

FIG. 5 illustrates excitory electrode 30 with an interdigitating pattern of positive and negative surface electrodes. When the electrodes are being used to impose a current driven mechanical stress in cartilage, a current density is created in the tissue.

Figure 6:
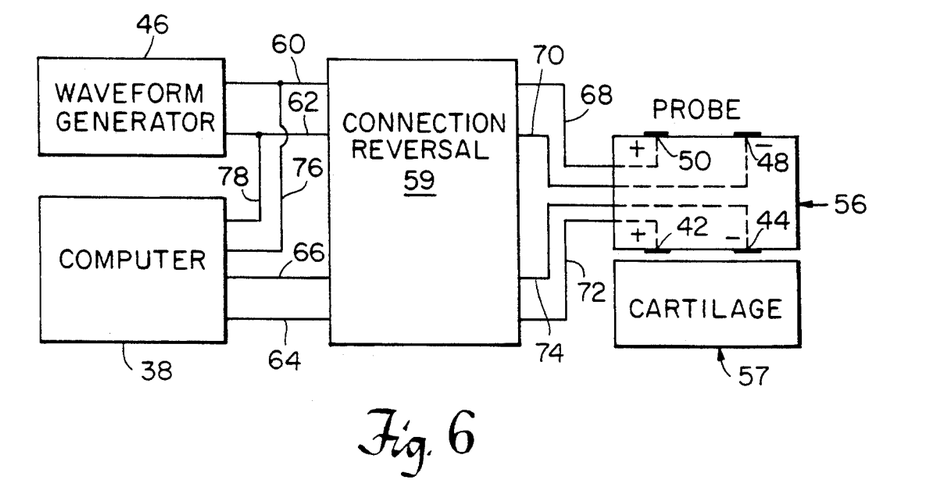
FIG. 6 is a block diagram illustrating a system for diagnosing degenerative changes in cartilage tissue.

As shown in a schematic representation of a system for diagnosing degenerative changes in cartilage tissue in FIG. 6, computer 38 is used to control the electromechanical transducer and to take data in real time therefrom. electrode 42, 44 of system probe 56 is connected by wires connection reversal box 59. A current is passed from waveform generator 46 into the tissue via positive electrode 42 and out through negative electrode 44. Electromechanical transducer electrodes 48, 50 are also connected to connection reversal box 59.

In FIG. 6, a voltage is applied from waveform generator 46 through electrodes 42, 44 contained in system probe 56. The resulting current generated stress is measured by electromechanical transducer. Alternatively, the electromechanical transducer lines can be transposed, and the electromechanical transducer can then apply a mechanical stress to the tissue. The resulting stress-generated streaming potential is measured by the electrode. In one embodiment, connection reversal box 59 allows transposition of the lines. The circuits are formed with lines 60, 62 connected to lines 72, 74, and lines 64, 66 connected to 68, 70 respectively, which can measure a mechanical force at electromechanical transducer 52 which is generated by an electrical current from electrode 54 directed into cartilage 57. Alternatively, connection reversal box 59 can allow the transposition of the lines to form circuits with lines 60, 62 connected to lines 70, 68 and lines 64, 66 connected to lines 74, 72, respectively, which can measure at electrodes 54 an electrical streaming potential generated by a mechanical force which is directed into cartilage 57 by electromechanical transducer 52. Lines 76, 78 from computer 38 are connected to lines 60, 62, respectively, allowing computer 38 to monitor or control the signals generated and received by waveform generator 46. The waveform voltage and streaming potential signals or the current waveform and current generated stress signals are then digitized, recorded and analyzed by computer 38 with a program algorithm.

Figure 7:
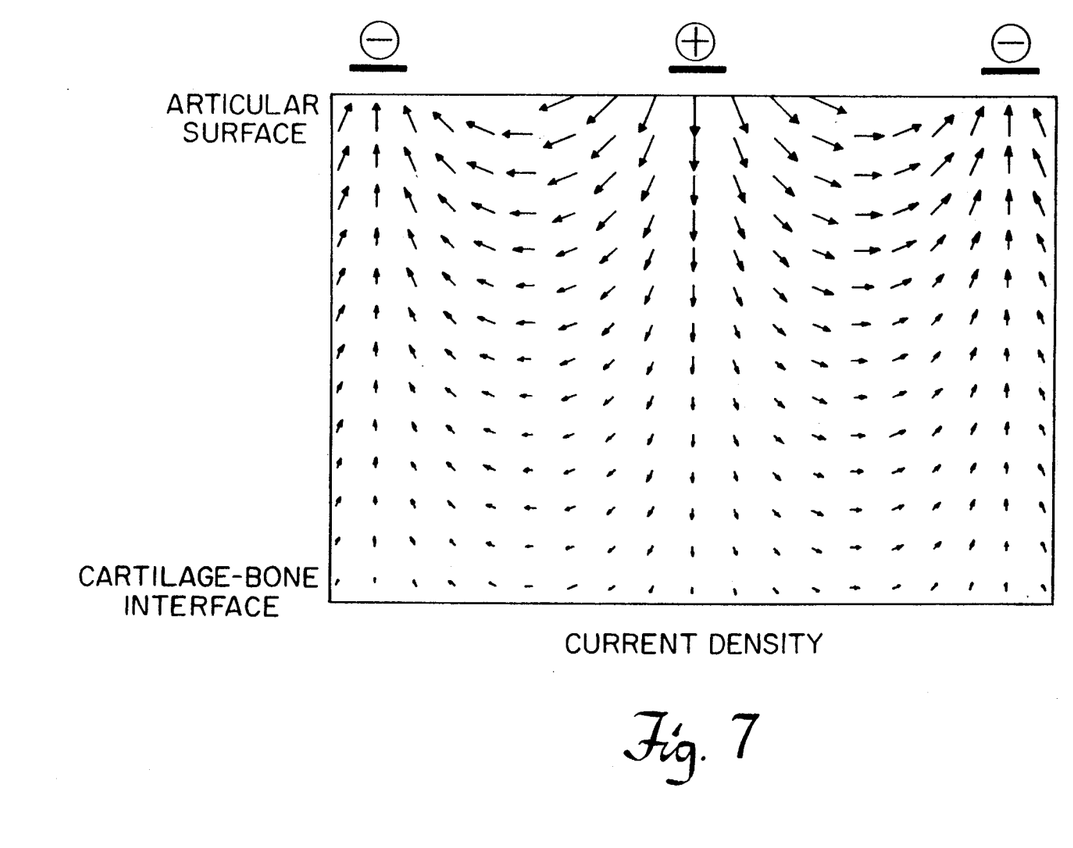
FIG. 7 is a schematic diagram illustrating the passage of current from the surface electrodes into cartilage tissue and the resulting current density.

FIG. 7 is a diagrammatic representation of current being applied to a cross-section of cartilage by the surface electrode and the resulting current density lines. The spatial wavelength is defined as twice the distance between two adjacent electrode strips. For a given electrode geometry and current amplitude applied to the electrodes, the current density is higher nearer the electrodes. From FIG. 7, this can be visualized as longer and thicker arrows. As the current is increased in amplitude from the surface electrodes, the current density through the tissue is increased proportionately. Conversely, as the applied current is decreased, the current density arrows would be smaller and shorter. With regard to frequency of current, the inverse is true. A higher frequency results in smaller and shorter arrows, as well as, less penetration of the current through the tissue. A lower frequency causes greater penetration of the current through the tissue. A longer wavelength results in greater penetration of current into the tissue; all other parameters remain the same.

Figure 8:
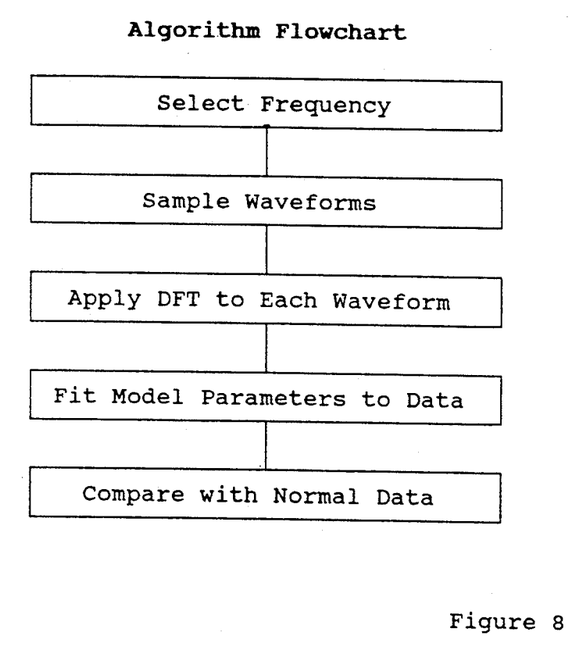
FIG. 8 is a schematic flow chart illustrating one embodiment of the steps of an algorithm used to interpret the viability of tissue.

FIG. 8 displays the program algorithm as used by the computer. In the first step, an excitation frequency is selected for the waveform generator. In the second step, the computer digitizes the electrical current and the stress signals from the electromechanical transducer at a frequency which is an exact multiple of the excitation frequency set in the waveform generator. In the third step after one or more complete cycles have been digitized and recorded, the computer does a discrete Fourier transform (DFT) to each waveform to yield a vector representing the magnitude and phase of each waveform.

The viability of the tissue can be determined given the magnitude and phase of each waveform. In the fourth step, a model is calculated based on the data that is output. In one embodiment, the simple ratio of stress output to current input magnitudes can yield a single "figure of merit" for the tissue electrokinetic response. In the fifth step, "the figure of merit" can then be compared to a table of previously obtained values for clinically normal and degraded tissue.

In another embodiment, data are obtained from several different frequencies or spatial wavelengths or both. A numerical fit of the parameters in Equations 1 through 8 is performed with respect to the data. The parameters include material moduli, hydraulic permeability and electrokinetic transduction coefficient. The numerical fit can be performed by the Marquardt method as described in Marquardt, "An Algorithm for Least-Squares Estimation of Nonlinear Parameters", *J Soc. Ind. Appl. Math.*, 11:431-41 (1963).

The surface probe employs surface electrical and mechanical signals that are periodic in both space and time. Spatially, the functions are approximately two-dimensional, varying with depth and with one surface dimension, and independent of the orthogonal surface dimension (e.g., a standing wave of imposed potential or displacement). By varying the imposed temporal frequency and the spatial wavelength of the input stimulus along the surface, it is possible to "tune" to specific depth within the tissue and thereby characterize the extent of focal degeneration even though only surface transducers and detectors are used.

Figure 9:
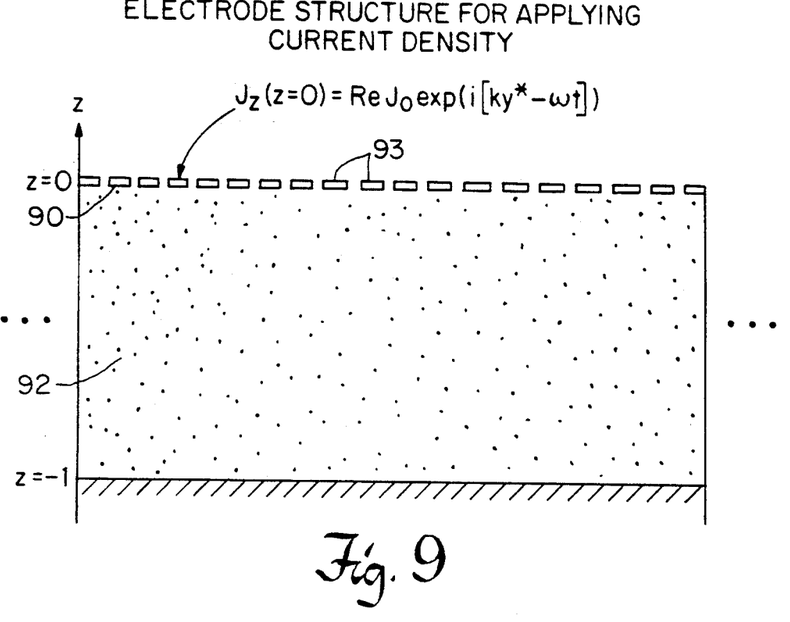
FIG. 9 is a cross-sectional view of cartilage and an electrode structure for applying current density to tissue and detecting mechanical stress.

A spatially varying electrical excitation is applied by interdigititating grid 93 to the surface 90 of the cartilage 92 and the resulting mechanical stress is measured simultaneously at the surface (FIG. 9). The experimental parameters are defined such that there is no vertical motion $u_2$, of the solid matrix and no relative normal fluid flow $U_z$ at the upper cartilage surface (z=0) within the extent of the electrode structure. The flat, multilayered electromechanical transducer is used to measure the spatially periodic mechanical stress generated at the surface by the applied current. This probe satisfies the displacement and fluid boundary conditions above, and also supports the electrode array. These constraints are met by bonding a patterned array made from a piezoelectric film onto an insulating substrate. The silver chloride array then is bonded on top of the piezoelectric film. A commercially available film which has an appropriate dynamic range of $10^{-5}$ to $10^8$ N/m$^2$ and a board band frequency response from dc to 1 GHz. In addition, a patterned array of this film can be fabricated with a strip width as small as 25 $\mu$m and inter-strip spacing of 100 $\mu$m. Since cartilage thickness varies, a series of arrays can be fashioned to probe short, middle and long wave responses.

Figure 10:
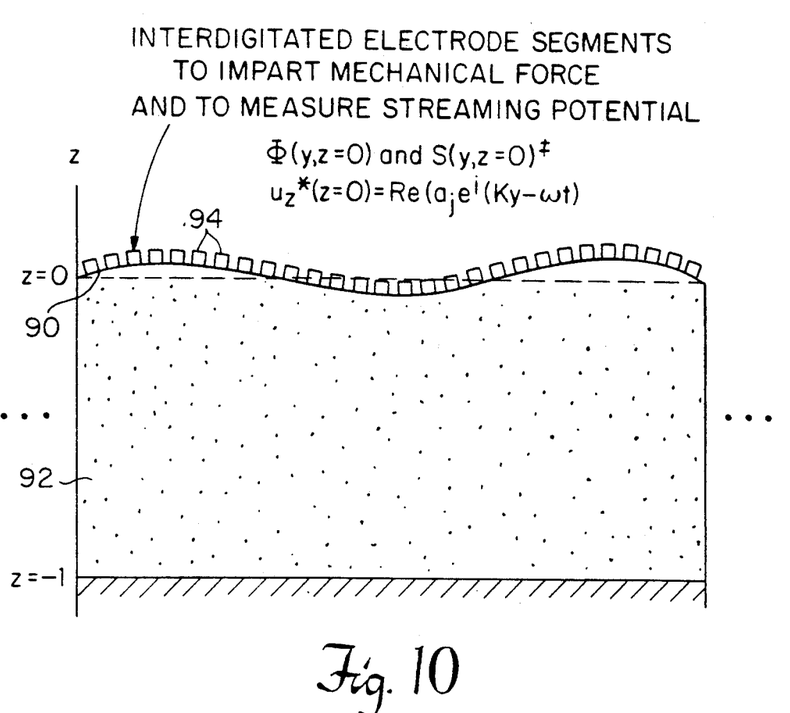
FIG. 10 is a cross-sectional view of cartilage and an electrode structure for applying mechanical displacement to the tissue for detecting electrical potential.

In another embodiment, an array of piezoelectric or electromechanical transducers 94 is constructed to impose the desired displacement on the cartilage surface 90 (FIG. 10). Each transducer has its own drive so that a spatially varying displacement can be imposed. In this scheme, a grid of potential sensing silver chloride electrodes can be attached to the sides of the transducers in contact with cartilage surface 90.

A computer system is used to control the transducer and to take data in real time from the electromechanical transducer electrode arrays. Since the measured response is at the same (temporal) frequency and spatial wavelength as the excitation, phase-lock detection and Fourier decomposition at the excitation frequency is used to find the amplitude and phase of the response (during use). An additional advantage of using an imposed spatial wavelength is the increased sensitivity obtained by measuring the response at the same wavelength. Differential amplification of the measured response between the "peak" and "valley" of the imposed spatial periodic waveform should greatly enhance the signal-to-noise ratio.

The measured streaming potential and current generated stress is first related to intrinsic, macroscopic material properties of cartilage. Linear electrokinetic transduction at each position in the tissue can be described in the non-equilibrium thermodynamic coupling laws that relate gradients in fluid pressure $P_f$ and potential V to relative fluid velocity U and current density J, $$\begin{bmatrix} U \\ J \end{bmatrix} = \begin{bmatrix} -k_{11} & k_{12} \\ k_{21} & -k_{22} \end{bmatrix} \begin{bmatrix} \nabla P_f \\ \nabla V \end{bmatrix} \quad (9)$$

where $k_{11}$ is the short-circuit hydraulic permeability, $k_{22}$ is the electrical conductance, and $k_{12}$ and $k_{21}$ are the electrokinetic coupling coefficients equal to each other by Onsager reciprocity.

The important intrinsic material properties that characterize the macroscopic behavior of cartilage are:
a) "pure mechanical" parameters: $k_{11}$ and the equilibrium elastic moduli (e.g., Lame coefficients),
b) "pure electrical" parameters: $k_{22}$, and
c) electromechanical coupling coefficients: $k_{12}=k_{21}$.

An appropriate and sufficient combination of amplitude and phase measurements (e.g., streaming potential, current generated stress and conductance) can be used to compute all the above material properties.

A layered model that accounts for variation of tissue properties with depth has also been formulated for the case of uniaxial compression (Frank et al., "Advances in Bioengineering", *Am. Soc. Mech. Eng.*, pps. 5-6, Nov. 19-22, 1988). Such variations are important for surface detection of non-uniform cartilage degeneration. Therefore, the surface periodic model is extended in an analogous manner to incorporate material non-uniformities. This further extension is valuable for the use of variable wavelength and frequency stimuli to detect and localize cartilage degeneration. Therefore, the approach of comparing normal cartilage to various stages of degeneration is made via a comparison of these intrinsic parameters. Normal values from a statistically significant, cross-sectional sampling are determined for each type of tissue, under both in vivo and in vitro conditions.

It is important to note that the "pure mechanical" parameters (elastic moduli, permeability $k_{11}$) and "pure electrical" parameters ($k_{22}$) are far less sensitive to degradative loss of proteoglycan molecules than the electrokinetic parameter $k_{12}$ and $k_{21}$. Since $k_{12}$ and $k_{21}$ are proportional to matrix charge density, loss of all proteoglycans decreases $k_{12}$ and $k_{21}$ from their normal value to zero. In contrast, $k_{11}$, $k_{22}$ and the equilibrium moduli are known to change by only a factor of two (A. J. Grodzinsky, Ibid (1983); Eisenberg et al., Ibid (1985)). Hence, the "dynamic range" of $k_{12}$ and $k_{21}$ in terms of molecular composition is far greater.

Therefore, the electromechanical spectroscopy approach proposed here focuses on $k_{12}$ and $k_{21}$. This approach is a far more sensitive indicator of early cartilage degeneration than purely mechanical or electrical tests (e.g., mechanical indentation or dielectric spectroscopy). (Eisenberg et al., "The Swelling of Articular Cartilage: Electromechanochemical Forces", *Trans. 1984 Orthop. Res. Soc.*, Atlanta, Ga., Feb. 7-9, p. 31 (1984); Grodzinsky, *Proc. 37th Conf. on Med. Biol.*, Los Angeles, Calif. p. 342, Sep. 17-19, 1984; Kavesh et al., *Proc. Bioelec. Repair and Growth Soc.*, Kyoto, Japan, p. 9, Nov. 5-8, 1984; Gray et al., *Proc. Bioelec. Repair and Growth Soc.*, Kyoto, Japan, p. 46, Nov. 5-8, 1984).

A principal use for this invention is its use as a diagnostic probe to assess the chemical, electrical and mechanical properties of cartilage. The purpose of the probe is to diagnose the viability of cartilage during arthroscopic examination of an articular joint. This aids detection of the early onset of joint disease, such as, which occurs in osteoarthritis.

In addition to the application of the surface probe in detecting cartilage degeneration, other biological applications exist in tissue repair and replacement. For example, the need for transplantation of articular cartilage, menisci, ligaments, muscle, and other tissues has necessitated development of suitable preservation and storage methods. The electromechanical surface probe provides a nondestructive means for characterizing the ability of transplant tissues to maintain their functional and molecular integrity following (cryo) presentation and storage, and as a means for monitoring the continued viability of the tissues after transplant.

The surface probe also has non-biological applications to materials in which electrical fields can induce deformation, such as, with polyelectrolytic gels and membranes.

Exemplification

The femoropatellar groove region of the distal femur of adult bovine knee joint was surgically removed and prepared for testing. The joint surface contained regions of reasonably flat cartilage approximately 1-3 $cm^2$ in area. During the process, the cartilage surface of the femoropatellar groove was kept free of blood by rinsing with phosphate buffered saline. For testing, the joint was mounted in a jig. The cartilage surface was equilibrated in buffered saline containing protease inhibitors to prevent natural degeneration and loss of matrix macromolecules that would otherwise occur gradually during testing over a several hour period. (The inhibitor solution includes 0.1M 6-aminohexanoic acid, 0.1M disodium EDTA, 0.001M benzamidine hydrochloride, 0.001M phenylmethylsulphanyl fluoride and 0.01M N-ethylmaleimide). These conditions simulate and in vivo environment.

Figure 11:
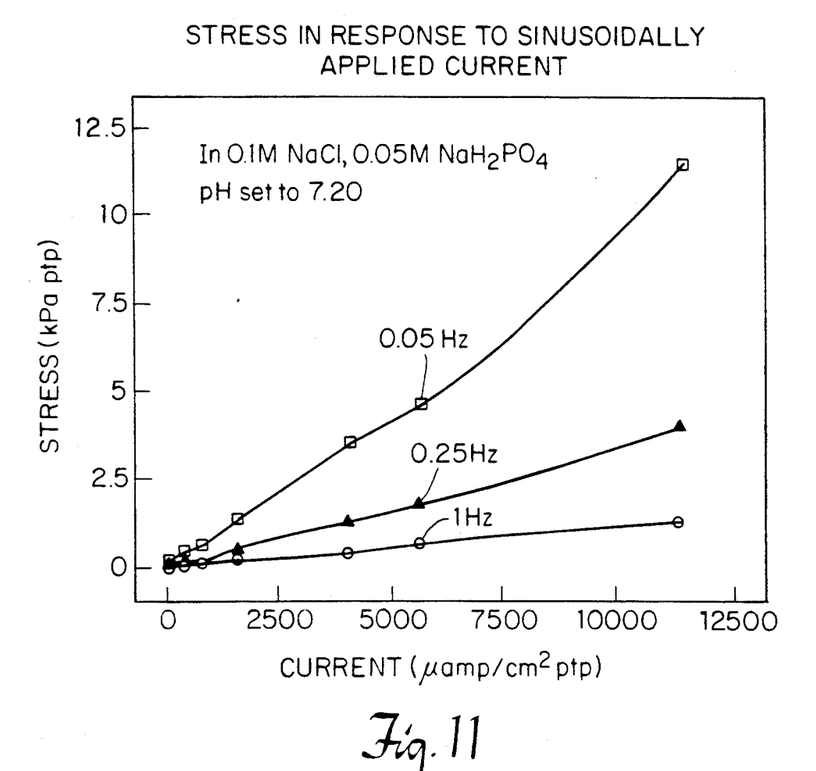
FIG. 11 is a graphic representation of detected mechanical stress of cartilage in response to a surface application of current density and the effect of increasing current frequency.

After the joint was mounted an equilibrated with buffer solution, the surface probe was positioned on the cartilage surface. Further, a series of increasing current densities was applied to the cartilage surface at three different frequencies, 0.05, 0.25 and 1.00 Hz. Secondly, the resultant stress was measured after each application of current. As seen in FIG. 11, as the applied current was increased, the resultant mechanical stress also increased. The effect of increasing frequency had the converse effect and decreased the resulting mechanical stress.

Equivalents

Those skilled in the art will recognize, or be able to ascertain using no more than routine experimentation, many equivalents to the specific embodiments of the invention described specifically herein. Such equivalents are intended to be encompassed in the scope of the claims.

We claim:

1. A surface probe for use in detecting the degree of degeneration in mammalian tissue, comprising a self-contained unit having mounted thereon in combination with each other:
   a) surface probe means for applying to a surface of the mammalian tissue a force which affects an electrokinetic parameter indicative of the amount of charged specie involved in tissue degeneration; and
   b) surface detection means for detecting said electrokinetic parameter at the same surface of the mammalian tissue where said force is applied.

2. A surface probe of claim 1 wherein said surface probe means for applying comprises means for applying an electrical force into said tissue and said surface detection means for detecting said electrokinetic parameter comprises a mechanical stress detector.

3. A surface probe of claim 2 wherein said surface probe means for applying has electrodes for directing an electrical force into said tissue which comprise an interdigitating grid of conductive material.

4. A surface probe of claim 3 wherein the conductive material of said electrodes comprise a metal.

5. A surface probe of claim 4 wherein the conductive material of said electrodes comprise a metal salt.

6. A surface probe of claim 5 wherein said conductive metal salt of said electrodes comprises silver chloride.

7. A surface probe of claim 5 wherein the metal salt electrode has receiving means for receiving input from a time varying current source.

8. A surface probe of claim 7 wherein the surface detection means for detecting said electrokinetic parameter comprises a piezoelectric polymeric film.

9. A surface probe of claim 8 wherein said surface detection means for detecting said electrokinetic parameter has means for transmitting a current to a computer system for data acquisition and processing.

10. A surface probe of claim 8 further comprises means for electrically isolating the surface probe means for applying said electrokinetic parameter from the surface detection probe means for detecting said electrokinetic parameters.

11. A surface probe of claim 1 wherein said surface probe means for applying comprises means for applying a mechanical stress to said tissue and said surface detection means for detecting comprises a detector for stress-generated streaming potential.

12. A method for detecting the degree of degeneration in mammalian tissue, comprising:
   a) applying to a surface of the mammalian tissue a force which affects an electrokinetic parameter indicative of the amount of charged species involved in tissue degeneration of said mammalian tissue;
   b) detecting said electrokinetic parameter at the same surface of the mammalian tissue where said force is applied; and
   c) comparing the detected electrokinetic parameter values to a normal value for said tissue previously measured from clinically normal tissue to thereby detect the degree of degeneration in mammalian tissue.

13. A method of claim 12 wherein the force in step (a) is applied into said tissue at varying depths or thicknesses by using electrical currents of variable temporal frequency and a variable imposed spatial wavelength by means of selectable excitation of elecrode segments of an interdigitating conductive grid.

14. A method of claim 13 wherein the force in step (a) which affects an electrokinetic parameter and said step of detecting said electrokinetic parameter occurs simultaneously with the step of applying the force.

15. A method of claim 12 wherein the force in step (a) is applied to cartilage tissue of a mammal.

16. A planar, multilayered, surface probe for diagnosing degenerative changes in cartilage tissue, comprising:
   a) surface electrodes with an interdigitating grid of conductive material for application of electrical current to a cartilage surface;
   b) a first insulating sheet with its lower surface metalized for electrical grounding and said surface electrodes bonded to the upper insulating surface of said first insulating sheet;
   c) a second insulating sheet bonded to the metalized side of the first insulating sheet;
   d) a piezoelectric polymeric film for transduction of mechanical stress to electrical current, bonded to the second insulating sheet; and
   e) electrodes bonded to said film for transmitting electrical current generated by the piezoelectric polymeric film to a detector.

17. A system for diagnosing degenerative changes in cartilage tissue, comprising:
   a) a surface probe of claim 16 with means for mounting said probe to the surface of the tissue;
   b) a waveform generator, as a source of electrical current, connected with converters for transmitting electrical current between said generator and said surface electrodes of said surface probe, to the surface electrode of said surface probe; and
   c) a computer connected by connectors to surface electrodes and transmitting electrodes in said surface probe for controlling electromechanical input to the surface electrodes and processing electromechanical output from the transmitting electrodes.

* * * * *

UNITED STATES PATENT AND TRADEMARK OFFICE
CERTIFICATE OF CORRECTION

PATENT NO. : 5,246,013
DATED : September 21, 1993
INVENTOR(S) : Eliot Frank, Evan P. Salant and Alan J. Grodzinsky It is certified that error appears in the above-identified patent and that said Letters Patent is hereby corrected as shown below:

In Column 1, after line 2, insert --This invention was made with government support under Contract No. EET88-11371 by the National Science Foundation. The government has certain rights in the invention--.

Signed and Sealed this

Twelfth Day of April, 1994

Attest:

BRUCE LEHMAN

*Attesting Officer*     Commissioner of Patents and Trademarks